US011957612B2

(12) United States Patent
Buonagurio

(10) Patent No.: US 11,957,612 B2
(45) Date of Patent: Apr. 16, 2024

(54) FORWARD BENDING SUPPORT BRACE

(71) Applicant: Timothy Buonagurio, Santa Cruz, CA (US)

(72) Inventor: Timothy Buonagurio, Santa Cruz, CA (US)

(*) Notice: Subject to any disclaimer, the term of this patent is extended or adjusted under 35 U.S.C. 154(b) by 478 days.

(21) Appl. No.: 17/197,509

(22) Filed: Mar. 10, 2021

(65) Prior Publication Data

US 2021/0282957 A1 Sep. 16, 2021

Related U.S. Application Data

(60) Provisional application No. 62/987,851, filed on Mar. 10, 2020.

(51) Int. Cl.
A61F 5/02 (2006.01)
A61F 5/01 (2006.01)
A61F 5/37 (2006.01)

(52) U.S. Cl.
CPC ............ *A61F 5/028* (2013.01); *A61F 5/3715* (2013.01); *A61F 2005/0197* (2013.01)

(58) Field of Classification Search
CPC .................... A61F 5/028; A61F 5/3715; A61F 2005/0197; A61F 5/02; A61F 5/01; A61F 5/00; A61F 5/37
See application file for complete search history.

(56) References Cited

U.S. PATENT DOCUMENTS 5,176,622 A * 1/1993 Anderson ................. A61F 5/02 482/131
7,744,552 B1 * 6/2010 Babcock ................... A61H 3/00 602/19
2015/0335461 A1 * 11/2015 Kuromiya ................. A61F 5/01 248/550

FOREIGN PATENT DOCUMENTS

| DE | 202017003616 U1 * | 8/2017 | |
| DE | 102019130389 A1 * | 5/2021 | ........... A61F 5/0026 |
| JP | 2020151003 A * | 9/2020 | ............ A61F 5/01 |
| RU | 195142 U1 * | 1/2020 | ............ A61F 5/00 |
| WO | WO-2011036906 A1 * | 3/2011 | ............ A61F 5/01 |
| WO | WO-2013106532 A1 * | 7/2013 | ............ A61F 5/01 |
| WO | WO-2014054097 A1 * | 4/2014 | ............ A61F 5/02 |
| WO | WO-2017217869 A1 * | 12/2017 | ............ A61F 5/028 |
| WO | WO-2021187973 A1 * | 9/2021 | ........... A61F 5/0102 |

* cited by examiner

Primary Examiner — Tarla R Patel
(74) Attorney, Agent, or Firm — SOQUEL GROUP LLC; Robert E. Blumberg

(57) ABSTRACT

The invention is a brace that secures to a person's chest, waist and legs. The brace includes a chest frame that supports the anterior chest and and a thigh frame that supports the anterior thighs where the two frames are pivotably connected to each other. In addition, an extension spring links the torso frame and the thigh frame such that when a user is bending over, i.e. flexed or in a state of flexion, in which gravity is exerting a greater downward force on the torso, a counter-force is exerted on the person's chest, with the counter-force increasing in magnitude as the degree of flexion at the waist increases.

11 Claims, 5 Drawing Sheets

FORWARD BENDING SUPPORT BRACE

BACKGROUND

Field of Art

This invention generally relates to the field of physiotherapy and medical equipment. Specifically, it provides devices and methods to support the lower back with a brace that provides an active counter-force.

BACKROUND OF THIS INVENTION

Lower back pain and disability are extremely common, and the incidence of these afflictions increase with conditions that require individuals to remain flexed at the waist for extended periods of time. For example, field and farm workers spend much of their working day in a bent over position as they perform their work. This position places significant stress on the lower lumbar spine, particularly in the $L_5$-$S_1$ spinal vertebrae region, as that region lies at the apex of the vertical to horizontal transition as a person bends forward at the waist.

Many braces exist that offer lower back support. These braces generally apply a circumferential compressive force to a person's midsection, providing increased intra-abdominal pressure to lift and support the lower spine. However, these braces are insufficient in preventing the development of debilitating lower back issues, and the incidence of lower back injury and pain is high in persons whose upper bodies are bent forward for prolonged periods of time.

Thus, it would be desirable to provide a brace to support a person who, typically for purposes of work, maintains a bent over position for longer than normal periods of time. Such a device would relieve tension and pressure from the lower lumbar spine.

SUMMARY

The subject invention is a forward bending support brace. Its goal is to relieve tension and pressure from structures of the thoracic and lumbar spine including muscles, ligaments, intervertebral discs and nerves.

The invention is a rigid frame assembly that may be secured to a person's chest, waist and legs. Embodiments include a portion that supports the anterior chest, referred to as a torso frame, and a portion that supports the anterior thighs, referred to as a thigh frame, where the two portions are pivotably connected to each other. In addition, an extension spring links the torso frame and the thigh frame such that when a user is bending over, i.e. is flexed or in a state of flexion, in which gravity is exerting a greater downward force on the torso, a counter-force is exerted on the person's chest, with the counter-force increasing in magnitude as the degree of flexion at the waist increases. In certain embodiments, the counter-force is applied through a chest pad attached to the torso frame.

BRIEF DESCRIPTION OF DRAWINGS

Non limiting and non exhaustive embodiments of the present invention are described with reference to the following drawings. In the drawings, like reference numerals refer to like parts throughout the various figures unless otherwise specified.

The figures depict embodiments of the present invention for purposes of illustration only. One skilled in the art will readily recognize from the following discussion that alternative embodiments of the device and structures illustrated herein may be employed without departing from the principles of the invention described herein.

DETAILED DESCRIPTION

The invention now will be described more fully hereinafter with reference to the accompanying drawings, which form a part hereof, and which show, by way of illustration, specific exemplary embodiments by which the invention may be practiced. This invention may, however, be embodied in many different forms and should not be construed as limited to the embodiments set forth herein; rather, these embodiments are provided so that this disclosure will be thorough and complete, and will fully convey the scope of the invention to those skilled in the art. Among other things, the invention may be embodied as devices and methods, and systems. The following detailed description is, therefore, not to be taken in a limiting sense.

The subject invention is a support brace that is intended to relieve tension and pressure from structures of the spine while a person is bending over. By doing this the invention decreases the damage inflicted to these structures and ultimately decreases pain and prevents injury. The invention has especial application for field workers that pick fruits and vegetables that grow on or near the ground. However, the invention has other uses and its use is not limited to field workers.

As used herein the term "user" refers to a person that is wearing the subject invention.

Figure 1A:
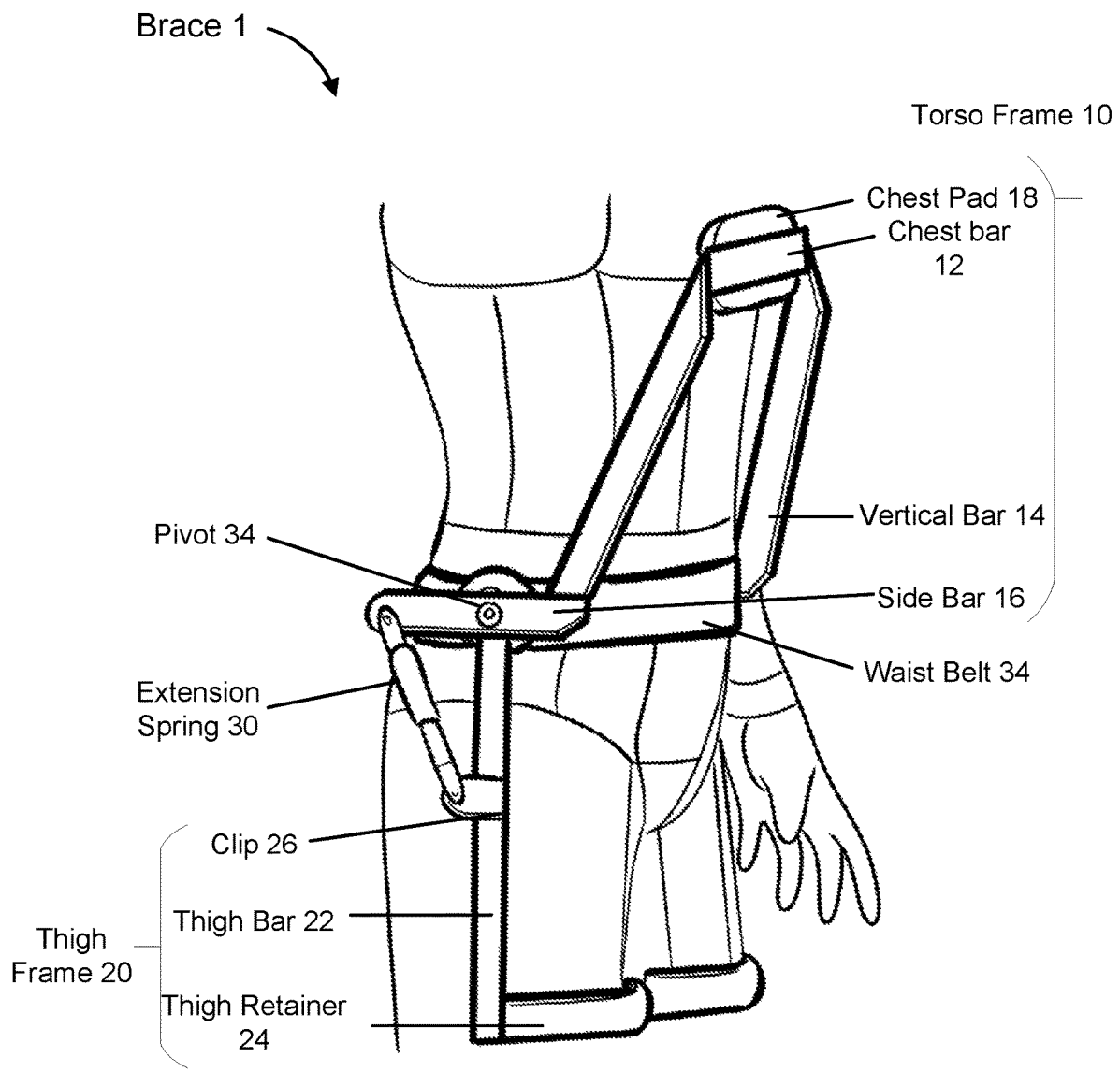
FIG. 1A illustrates a side view of a person wearing a front bending support brace.

FIG. 1A illustrates a a side view of a user wearing an embodiment of a front bending support brace 1. Support brace 1 includes the following components:

(1) A torso frame 10, which, when brace 1 is worn by a user, presses against t user's chest at the top, exerting a counter-force to the pull of gravity on the user's torso when he/she bends forward, and which is pivotably connected with a lower thigh frame 20. Torso frame 10 has a top, a bottom, a right side and a left side.

(2) Thigh frame 20, which, when brace 1 is worn by a user, presses against the user's legs at the bottom of brace 1, and which is pivotably connected with torso frame 10. Thigh frame 10 has a separate right side and left side which connect to torso frame on the respective right and left sides via a pivot 34 on each side.

(3) An extension spring 30 (or simply spring 30) attaches at the top to torso frame 10 and at the bottom to thigh frame 20 via a clip 26. There is an extension spring 30 on both the right and left side of brace 1.

(4) A waist belt 34 that serves to attach torso frame 10 and thigh frame 20 to the user's body.

Torso frame 10 has three principal sections: a torso frame side bar 16 (or simply side bar 16) on either side of the user's body that when worn by a user is substantially horizontal, and is positioned close to the user's waist; a torso frame vertical bar 14 (or simply vertical bar 14) on either side of the users's torso that angles upward to reach the approximate height of the user's chest; and a single chest bar 12, which is horizontal, at approximately the height of a user's chest and is positioned in the front of the chest. Thus, the three different sections of torso frame 10 are composed of five distinguishable structural elements or portions.

The five structural elements of torso frame 10, i.e. chest bar 12, the two vertical bars 14 and the two side bars 16 may be an integral structure, such as a single piece of sheet metal; or it may consist of five separate elements that are fixedly attached, e.g. through welds or bolts. The material of the various elements may be steel, sheet metal, fiberglass, carbon fiber, plastic or another material that is suitably durable, strong.

In certain embodiments, chest bar 12 contacts the user's chest when brace 1 is worn. In other embodiments, as illustrated in FIG. 1A, a chest pad 18 attaches on the inside of chest bar 12 between chest bar 12 and the user's chest. Chest pad 18 typically provides a softer contact surface than chest bar 12. Chest pad 18 is typically constructed of a soft material such as gel pad, foam pad, elasticized plastic, or rubber.

There is one thigh frame 20 for the user's right thigh and another one for the user's left thigh. Each of the two thigh frames 20 has three principal sections: a thigh bar 22 that descends vertically on the side of a thigh; a thigh retainer 22 that that fits over an anterior thigh, typically above the knee, and, in certain embodiments, a clip 26 that enables extension spring 30 to connect to the thigh frame 20. In certain embodiments, extension spring 30 attaches directly to thigh bar 22, in which case clip 26 is not required.

The six structural elements of thigh frame 20, i.e. two thigh bars 22, two thigh retainers 24, and two clips 26 may be an integral structure, such as a single piece of sheet metal; or it may consist of separate elements that are fixedly attached, e.g. through welds or bolts. The material of the various elements may be steel, sheet metal, fiberglass, carbon fiber, plastic or another material that is suitably durable and strong.

Thigh retainer 24 may be a made of a strong, durable material, or it may be a softer material that makes flexible contact with the anterior thigh, such as gel pad, foam pad, elasticized plastic, or rubber. In other embodiments, not depicted, a thigh pad made of a soft material mounts inside thigh retainer 24, analogous to chest pad 18, between thigh retainer 24 and the anterior thigh such that only the thigh pad contacts the anterior thigh.

Torso frame 10 and thigh frame 20 connect, or attach, at a pivot 34 on each side of the body. Pivot 34 may be a bolt or other connecting mechanism that enables torso frame 10 and thigh frame 20 to rotate independently in the forward and backward directions. For example, when the user steps forward with the right leg, the right thigh frame 20 will move forward. This movement may have a minimal added resistance due to the right pivot 34 and the right extension spring 30, but the movement should not be substantially be impeded by brace 1.

In certain embodiments waist belt 34 also attaches to torso frame 10 and thigh frame 20 on the right and left sides of the user via pivot 34. Waist belt 34 serves to attach brace 1 to the user's body. Waist belt 34 typically includes a tightening mechanism, such as a buckle, to tighten it around the user's waist.

Extension spring 30 typically has a minimal preload tension when it is at the minimal extension; this occurs when the user stands upright. When the user bends forward extension spring 30 is pulled upward. Conversely, when the user steps forward with a leg spring 30 is pulled downward. In certain embodiments, extension spring 30 is a commercial product. For example, in certain embodiments extension spring 30 is a hydraulic spring, hydraulic gas spring, or gas spring. Such a spring may have a single acting cylinder, also referred to as a one way cylinder in which the pressure and extension stroke occur on one side of a piston; alternatively, a double acting cylinder, also referred to as two way cylinder, where extension and pressure occur on both sides of the piston. When a hydraulic spring is used, extension spring 30 includes a suitable end fitting, such as an end fitting loop or end fitting bracket, which attaches at one end to side bar 16 and at the other end to clip 26 or directly to thigh bar 22. In other embodiments, elastic or rubber cords, bands, tubes, or resistance balls, may be used as extension springs 30. An advantage of this approach is that a variety of bands, cords, tubes or balss, each with a different level of tension can be inexpensively provided and the user can select the appropriate tension level.

Generally, it is desirable that extension spring 30 obey Hooke's law over a normal operating range or distance, i.e. that the force (F) needed to extend or compress extension spring 30 scales linearly, by a constant factor K, over a distance within its normal operating range. The operating range is dependent on the type of spring used. For example, in certain embodiments a normal operating range of 2 to 12 inches is desirable; in other embodiments a normal range of 4 to 8 inches may be desirable.

Figure 1B:
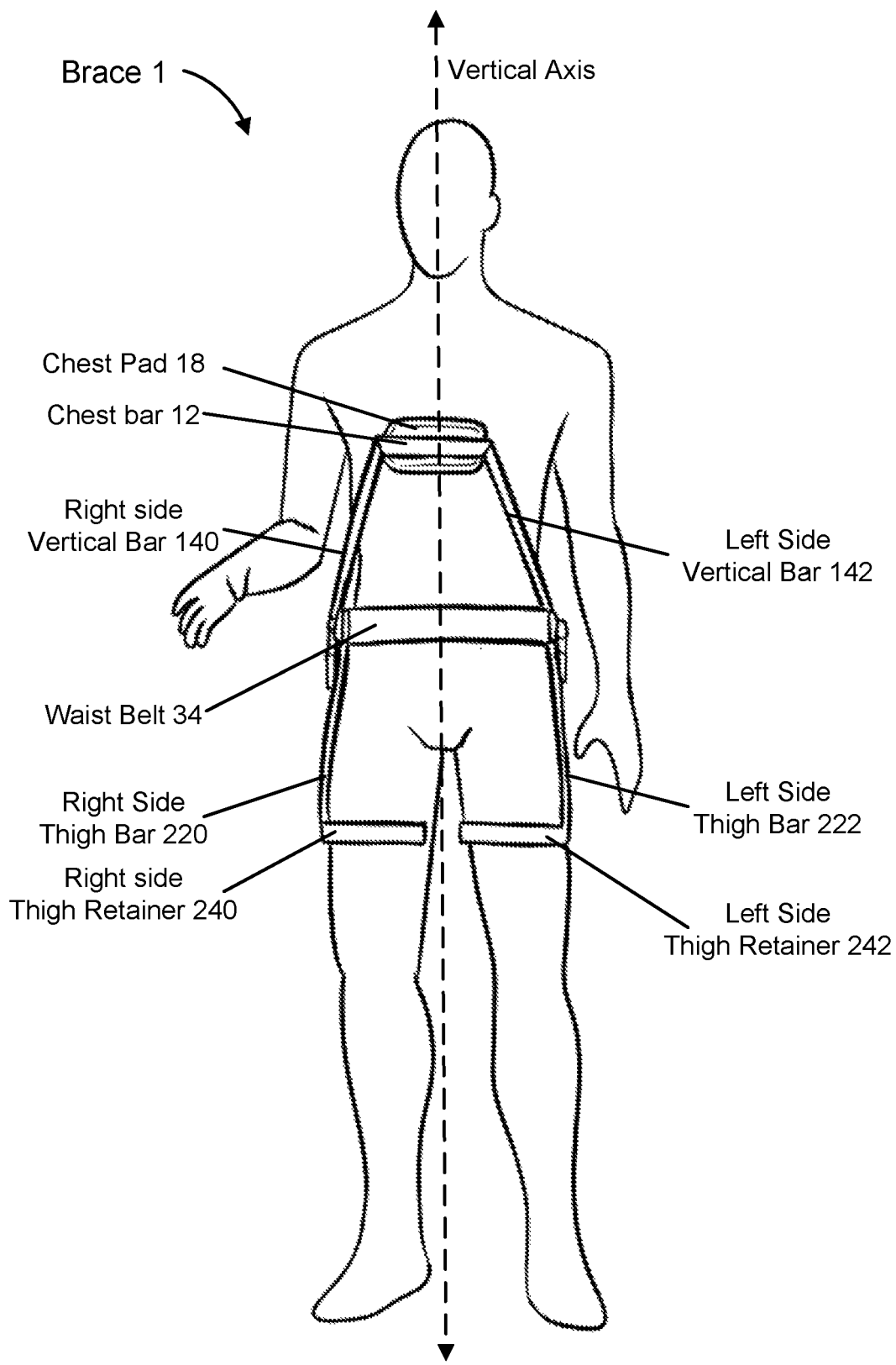
FIG. 1B illustrates a frontal view of a person wearing the front bending support brace.

FIG. 1B illustrates a frontal view of a person wearing the front bending support brace. As illustrated, brace 1 is vertically symmetric with respect to a center vertical axis. Thus, brace 1 includes a right side vertical bar 140 and a left side vertical bar 142, a right side thigh bar 220 and a left side thigh bar 222, and a right side thigh retainer 240 and a left side thigh retainer 242. Only a single chest pad 18 and a single waist belt 34 are used in this embodiments. In other embodiments, there may be a right and a left chest pad 18. Although, not depicted, there is an extension spring 30 on the right and left side and a clip 26 on the right and left side.

Figure 2A:
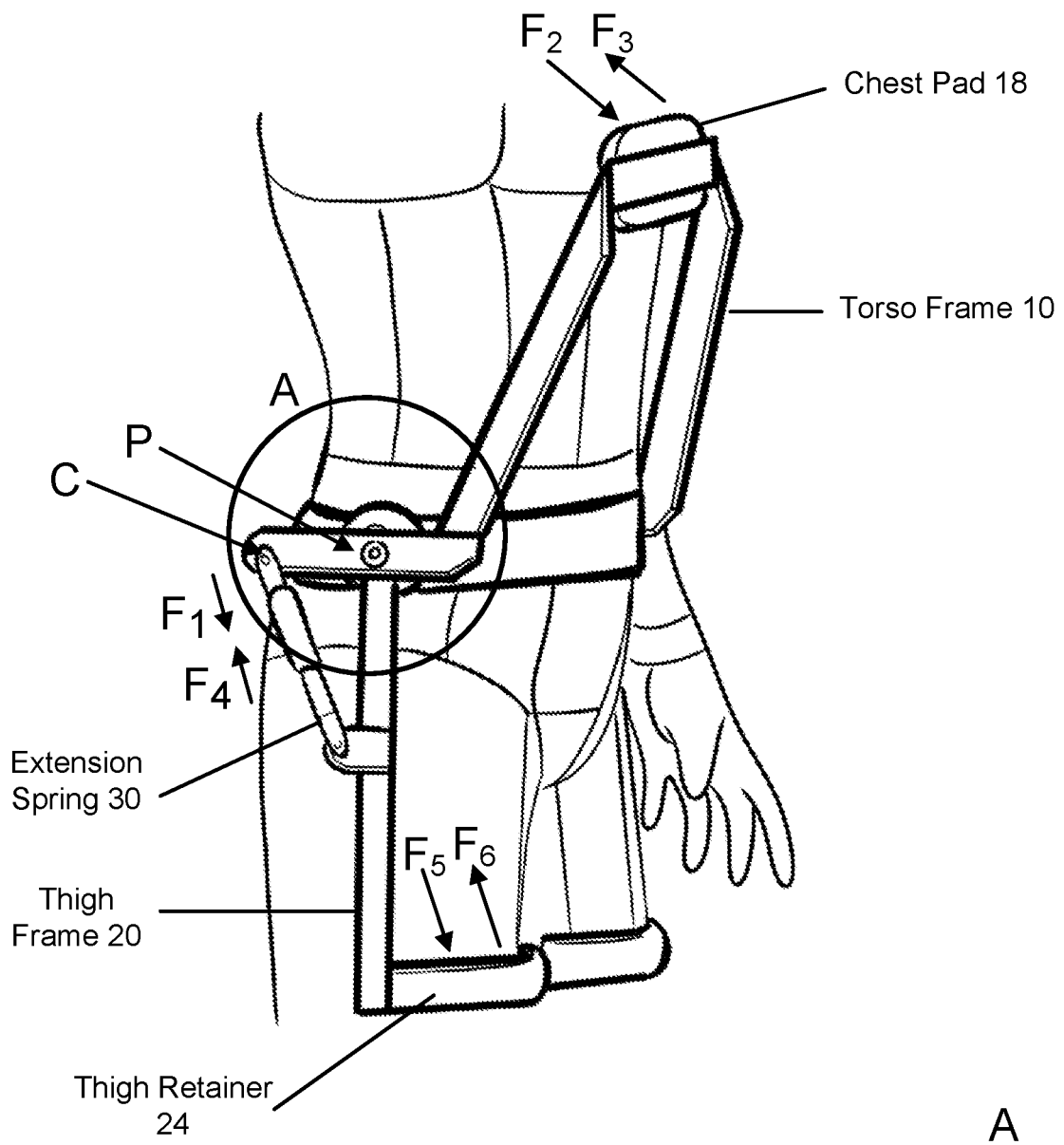
FIG. 2A illustrates the ways that forces are transmitted through the front bending support brace.

FIG. 2A illustrates the ways that forces are transmitted through brace 1. Extension spring 30 typically has a preset tension level that provides a slight downward force on side bar 16 at the point of connection, C. This has the effect of providing a counter-clockwise rotational, downward, force on torso frame 10 that provides some resistance through chest pad 18 that supports the user's chest. When the user bends over, he/she exerts a forward force, F2, against chest pad 18. Force F2 may be due in part to the thrusting force of the user's chest motion and in part due to the downward force of gravity on the torso. This force is transmitted to extension spring 30 through the clockwise rotation of torso frame 10 and has the effect of pulling upward, on extension spring 30 which increases the spring tension and results in a larger downward force F1. This results in a counter-force F3 being transmitted through torso frame 10 to the user via chest pad 18, thus counteracting, at least in part, downward force F2. Thus, an increased degree of flexion at the waist causes increased stretching of extension spring 30; this in turn results in a higher counter-force, F3, applied to the chest to support the lower back. The counter-force counters, at least in part, the effect of gravity that pulls the users torso downward as he/she bends forward.

Thus, brace 1 applies a counter-force to the user's chest that increases as the user flexes at the waist. For example, if a user is in a standing position, flexing at the waist is equivalent to bending forward from an upright position. When the user flexes at the waist, extension springs 30 apply a counter-force to the person's chest. The force applied to the chest partially unloads the downward force exerted by the upper body on the bent lumbar spine. The magnitude of the counter-force increases linearly with the degree of flexion at the waist, and the closer the person bends down towards the ground, the greater the resultant back support provided. The support force is related proportionately to the spring constant of the extension springs connected to the torso and thigh frames. In certain embodiments, the tension level of extension springs 30 may be adjusted to provide an increased or decreased level of back support.

Analogous to the counter-force, F3, generated against the user's chest, a counter-force, F6, can be generated against the thigh of the user, via thigh retainer 24. When the user steps forward or bends the leg, the thigh exerts a force F5 against thigh retainer 24. This moves thigh frame 20 forward and pull downward on extension spring 30. Extension spring 30 in turn exerts a counter-force F4 that, at least in part, counteracts the forward force F5 and results in the counter-force F6 being transmitted through thigh retainer 24 to the user's thigh.

It may be appreciated that brace 1 may be configured to exert a counter-force through both torso frame 10 and thigh frame 20; alterntiavely it may be configured to exert a counter-force only through torso frame 10 or thigh frame 20.

Figure 2B:
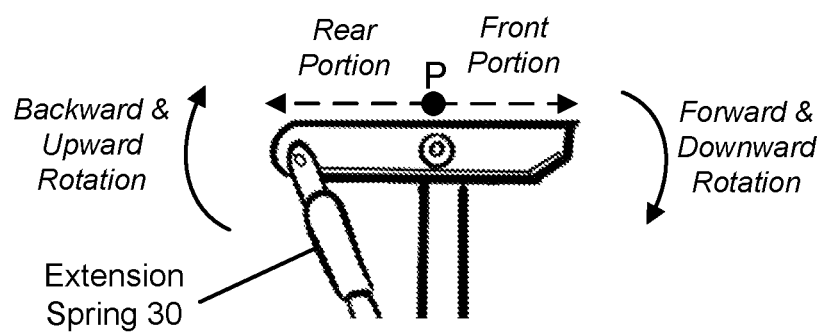
FIG. 2B illustrates the rotation of torso frame about a pivot point, P.

FIG. 2B is a closeup view of a portion of FIG. 2A, labeled A, that illustrates the rotation of torso frame about a pivot point, P. When the user bends forward, the portion of torso frame 10 to the right of the pivot point, P, referred to as the front portion, rotates forward and downward. At the same time, the portion of torso frame 10 to the left of the pivot point, P, referred to as the rear portion, rotates backward and upward. Thus, bending forward by the user results in extension spring 30 being pulled upward, resulting in a downward counter-force generated by extension spring 30.

Figure 3:
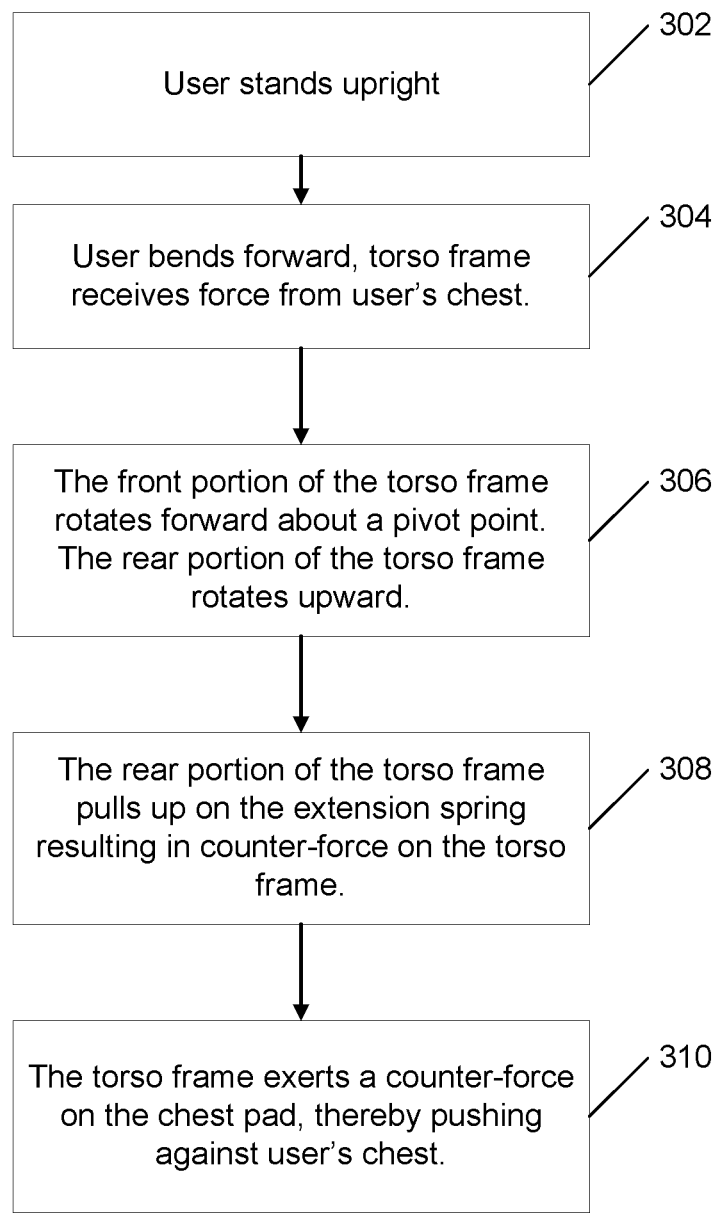
FIG. 3 is a flow diagram of a method of applying a counter-force to the chest of a person bending forward at the waist by a brace worn by the user.

FIG. 3 is a flow diagram of a method of applying a counter-force to the chest of a person bending forward at the waist by a brace worn by the user. At step 302, it is assumed that the user is standing upright. At step 304 the method is initiated with the user ends forward; in this event, the torso frame 10 receives a force that is transmitted from the user's chest to chest pad 18 and hence to chest bar 12.

At step 306, in response to receiving the force due to the user bending forward, the front portion of torso frame 10 rotates forward about pivot point P and the rear portion of torso frame 10 rotates upward.

At step 308, when the rear portion of torso frame 10 rotates up it pulls on extension spring 30, resulting in a counter-force being applied by extension spring 30 on the rear portion of torso frame 10.

At step 310, the counter-force applied by extension spring 30 onto torso frame 10 is transmitted to the chest pad which in turn pushes against the user's chest.

Figure 4:
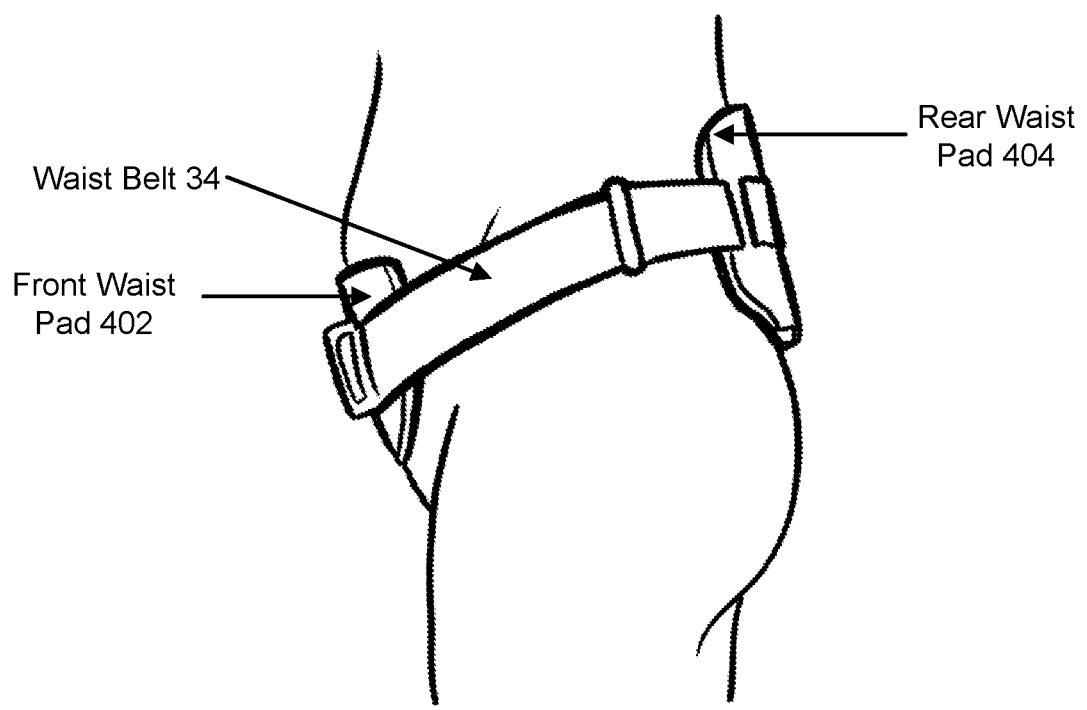
FIG. 4 illustrates an embodiment of the front bending support brace which has a front waist pad and a rear waist pad.

FIG. 4 illustrates an embodiment of brace 1 which has a front waist pad 402 and a rear waist pad 404 attached to waist belt 34. In certain embodiments, front waist pad 402 attaches in the front of waist belt 34 and rear waist pad 404 attaches in the rear of waist belt 34. It is understood that front refers to the user's front and rear refers to the user's backside or rear side.

Similar to chest pad 18, front waist pad 402 and rear waist pad 404 provide a flexible, softer contact than waist belt 34 and made be constructed of a material such as a gel pad, foam pad, elasticized plastic, or rubber. To protect against sweat, the waist pads may be covered with a water-resistant material such as plastic.

Upon reading this disclosure, those of skill in the art will appreciate still additional alternative structural and functional designs through the disclosed principles herein. Thus, while particular embodiments and applications have been illustrated and described, it is to be understood that the disclosed embodiments are not limited to the precise construction and components disclosed herein. Various modifications, changes and variations, which will be apparent to those skilled in the art, may be made in the arrangement, operation and details of the method and apparatus disclosed herein without departing from the spirit and scope defined in the appended claims.

What is claimed is:

1. A brace worn by a user that provides lower back support, comprising:
   a torso frame configured to contact the user at chest height;
   a thigh frame, pivotably attached to the torso frame, configured to contact the user's thighs;
   an extension spring, which attaches to both the torso frame and the thigh frame, configured to exert a counter-force on the torso frame when the user bends forward, wherein the counter-force is transmitted through the torso frame to the chest of the user; and
   a waist belt, configured to encircle the user's waist and which attaches to both the torso frame and the thigh frame, thus securing the brace to the user's body; and
   wherein the torso frame, thigh frame, and waist belt are attached by two pivot mechanisms, one configured to be waist height on the user's right side and one configured to be at waist height on the user's left side and wherein each of the two pivot mechanisms enables the torso frame to pivot forward and backward and also enables the thigh frame to pivot forward and backward.

2. The brace of claim 1 wherein the torso frame comprises the following members:
   a horizontal right side bar, configured to be disposed on the right side of the user at waist height;
   a right vertical bar, attached to the right side bar, that angles upward and attaches a chest bar;
   the chest bar, configured to be disposed horizontally, in front of the user's chest;
   a horizontal left side bar, configured to be disposed on the left side of the user at waist height; and
   a left vertical bar, attached to the left side bar, that angles upward and attaches to the chest bar.

3. The brace of claim 2 wherein the members of the torso frame form integral structure.

4. The brace of claim 3 where the integral structure is made of sheet metal, steel or plastic.

5. The brace of claim 2 wherein each of the members connect to form the torso frame.

6. The brace of claim 1 wherein each pivot mechanism is a bolt or rod.

7. The brace of claim 1 wherein the thigh frame comprises the following members:
   a vertical right thigh bar, configured to be disposed along the user's right thigh;
   a right thigh retainer, attached to the right thigh bar, configured to be disposed horizontally above the user's right knee;

a vertical left thigh bar, configured to be disposed along the user's left thigh; and a left thigh retainer, attached to the left thigh bar, configured to be disposed horizontally above the user's left knee.

8. The brace of claim 7 wherein the right thigh bar and the right thigh retainer are attached to form a right thigh frame and the left thigh bar and the left thigh retainer are attached to form a left thigh frame.

9. The brace of claim 7 wherein the thigh retainer is configured so that when the user moves his/her leg forward, the thigh presses against the thigh retainer causing the thigh frame to rotate forward and to pull the extension spring downward, resulting in an increased counter-force on the thigh retainer.

10. The brace of claim 1 wherein there is a chest pad attached on the chest bar.

11. The brace of claim 10 wherein the torso frame is configured to rotate forward when the user bends forward and presses against the chest pad causing the side bar to rotate upward and to lift the extension spring, resulting in an increased counter-force on the torso frame.

* * * * *